United States Patent
Ouchi et al.

(10) Patent No.: US 12,202,797 B2
(45) Date of Patent: Jan. 21, 2025

(54) METHOD FOR PRODUCING PYRROLE COMPOUND

(71) Applicant: Takeda Pharmaceutical Company Limited, Osaka (JP)

(72) Inventors: Takashi Ouchi, Osaka (JP); Giho Goh, Daejeon (KR); Sunmi Kim, Daejeon (KR); Jinsoon Choi, Daejeon (KR); Hunsoo Park, Daejeon (KR)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 18/132,677

(22) Filed: Apr. 10, 2023

(65) Prior Publication Data

US 2023/0322669 A1 Oct. 12, 2023

Related U.S. Application Data

(62) Division of application No. 17/350,013, filed on Jun. 17, 2021, now Pat. No. 11,649,206, which is a division of application No. 16/739,707, filed on Jan. 10, 2020, now Pat. No. 11,066,362, which is a division of application No. 15/739,877, filed as application No. PCT/JP2016/069258 on Jun. 29, 2016, now Pat. No. 10,570,091.

(30) Foreign Application Priority Data

Jun. 30, 2015 (JP) ................. 2015-131610

(51) Int. Cl.

| | |
|---|---|
| C07D 207/36 | (2006.01) |
| B01J 8/02 | (2006.01) |
| B01J 21/04 | (2006.01) |
| B01J 23/44 | (2006.01) |
| B01J 29/08 | (2006.01) |
| C07B 31/00 | (2006.01) |
| C07B 41/06 | (2006.01) |
| C07B 61/00 | (2006.01) |
| C07C 253/30 | (2006.01) |
| C07C 255/28 | (2006.01) |
| C07C 255/42 | (2006.01) |
| C07D 207/34 | (2006.01) |
| C07D 401/12 | (2006.01) |

(52) U.S. Cl.
CPC .......... *C07D 207/36* (2013.01); *B01J 8/0278* (2013.01); *B01J 21/04* (2013.01); *B01J 23/44* (2013.01); *B01J 29/08* (2013.01); *C07B 31/00* (2013.01); *C07B 41/06* (2013.01); *C07B 61/00* (2013.01); *C07C 253/30* (2013.01); *C07C 255/28* (2013.01); *C07C 255/42* (2013.01); *C07D 207/34* (2013.01); *C07D 401/12* (2013.01); *B01J 2523/67* (2013.01); *B01J 2523/68* (2013.01); *B01J 2523/69* (2013.01); *B01J 2523/824* (2013.01); *B01J 2523/828* (2013.01); *B01J 2523/847* (2013.01)

(58) Field of Classification Search
None
See application file for complete search history.

(56) References Cited

U.S. PATENT DOCUMENTS

| | | | |
|---|---|---|---|
| 3,849,457 | A | 11/1974 | Haag et al. |
| 4,500,721 | A | 2/1985 | Yamachika et al. |
| 5,081,321 | A | 1/1992 | Fukuhara et al. |
| 5,252,746 | A | 10/1993 | Lowen |
| 6,559,333 | B1 | 5/2003 | Brunelle et al. |

(Continued)

FOREIGN PATENT DOCUMENTS

| | | |
|---|---|---|
| CN | 102421753 A | 4/2012 |
| EP | 2402313 A1 | 1/2012 |

(Continued)

OTHER PUBLICATIONS

Eigenberger et al., Catalytic Fixed-Bed Reactors. Ullmann's Encyclopedia of Industrial Chemistry. Wiley-VCH Verlag Gmbh & Co. KGaA, Weinheim. pp. 1-3, (2015).

(Continued)

*Primary Examiner* — Samantha L Shterengarts
(74) *Attorney, Agent, or Firm* — McCarter & English, LLP; David G. Conlin

(57) ABSTRACT

The present invention provides a production method of a 3-cyanopyrrole compound possibly useful as an intermediate for pharmaceutical products. A production method of compound (II) including subjecting compound (I) to a reduction reaction, in which the aforementioned reduction reaction is continuous hydrogenation reaction in a fixed bed reactor filled with a supported metal catalyst. A production method of compound (III) including subjecting compound (I) to a reduction reaction followed by a cyclization reaction, in which the aforementioned reduction reaction is continuous hydrogenation reaction in a fixed bed reactor filled with a supported metal catalyst.

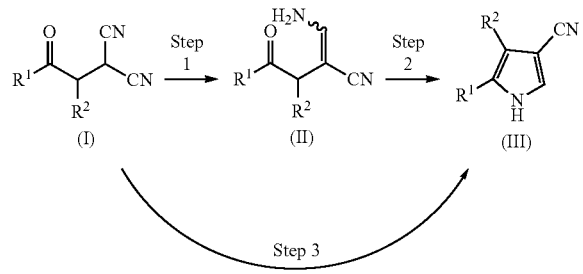

17 Claims, 2 Drawing Sheets

(56) References Cited

U.S. PATENT DOCUMENTS

| | | |
|---|---|---|
| 7,498,337 B2 | 3/2009 | Kajino et al. |
| 7,977,488 B2 | 7/2011 | Kajino et al. |
| 8,048,909 B2 | 11/2011 | Kajino et al. |
| 8,299,261 B2 | 10/2012 | Kajino et al. |
| 8,338,461 B2 | 12/2012 | Kajino et al. |
| 8,338,462 B2 | 12/2012 | Kajino et al. |
| 8,415,368 B2 | 4/2013 | Kajino et al. |
| 8,436,187 B2 | 5/2013 | Kajino et al. |
| 8,822,694 B2 | 9/2014 | Ikemoto et al. |
| 9,266,831 B2 | 2/2016 | Ikemoto et al. |
| 9,487,485 B2 | 11/2016 | Majima |
| 9,932,322 B2 | 4/2018 | Majima |
| 10,570,091 B2 | 2/2020 | Ouchi et al. |
| 11,066,362 B2 | 7/2021 | Ouchi et al. |
| 11,649,206 B2 | 5/2023 | Ouchi et al. |
| 2007/0060623 A1 | 3/2007 | Kajino et al. |
| 2007/0287865 A1 | 12/2007 | Arredondo et al. |
| 2008/0045749 A1 | 2/2008 | Arredondo et al. |
| 2008/0139639 A1 | 6/2008 | Kajino et al. |
| 2009/0143444 A1 | 6/2009 | Kajino et al. |
| 2009/0275591 A1 | 11/2009 | Kajino et al. |
| 2011/0028476 A1 | 2/2011 | Kajino et al. |
| 2011/0144161 A1 | 6/2011 | Kajino et al. |
| 2011/0301173 A1 | 12/2011 | Kajino et al. |
| 2011/0301174 A1 | 12/2011 | Kajino et al. |
| 2011/0306769 A1 | 12/2011 | Ikemoto et al. |
| 2012/0088797 A1 | 4/2012 | Kajino et al. |
| 2014/0135511 A1 | 5/2014 | Izawa et al. |
| 2014/0303378 A1 | 10/2014 | Ikemoto et al. |
| 2014/0343070 A1 | 11/2014 | Kajino et al. |
| 2016/0009646 A1 | 1/2016 | Majima |
| 2017/0008874 A1 | 1/2017 | Majima |
| 2018/0009746 A1 | 1/2018 | Ikemoto et al. |

FOREIGN PATENT DOCUMENTS

| | | |
|---|---|---|
| JP | 38-4339 | 4/1963 |
| JP | 41-6326 | 4/1966 |
| JP | 47-20083 Y1 | 7/1972 |
| JP | 52-33081 Y2 | 7/1977 |
| JP | 58-146527 U | 10/1983 |
| JP | 60-260569 A | 12/1985 |
| JP | 2-270829 A | 11/1990 |
| JP | 7-206784 A | 8/1995 |
| JP | 2001-158754 A | 6/2001 |
| JP | 2009-539858 A | 11/2009 |
| JP | 2013-40169 A | 2/2013 |
| WO | 1989/05286 A1 | 6/1989 |
| WO | 2005/039766 A1 | 5/2005 |
| WO | 2006/036024 A1 | 4/2006 |
| WO | 2007/026916 A1 | 3/2007 |
| WO | 2010/098351 A1 | 9/2010 |
| WO | 2014/133059 A1 | 9/2014 |

OTHER PUBLICATIONS

Nakabayashi et al., Thermal Energy Up-graded by Use of Cyclohexane Dehydrogeno-aromatization. Hydrogen Energy System. 1993;18(2):28-35.

Ouchi et al., Process Intensification for the Continuous Flow Hydrogenation of Ethyl Nicotinate. Organic Process Research & Development. 2014;18:1560-1566, with supplemental materials.

Oyamada et al., Continuous flow hydrogenation using polysilane-supported palladium/alumina hybrid catalysts. Beilstein J Org Chem. 2011;7:735-9.

Wang, Preparation of Catalysts for Selective Hydrogenation of Benzonitrile to Benzylamine. Shanghai University, Professional Master's Degree Thesis. 171 pages, May 2014.

Chinese Office Action for Application No. 201680048676.5, dated Jan. 6, 2020, 21 pages.

European Office Action for Application No. 16817957.0, dated Feb. 11, 2019, 10 pages.

European Office Action for Application No. 16817957.0, dated May 27, 2019, 11 pages.

International Search Report and Written Opinion for Application No. PCT/JP2016/069258, dated Sep. 20, 2016, 23 pages.

Japanese Office Action for Application No. 2020-188087, dated Oct. 12, 2021, 4 pages.

Barnett et al., Pyrrole chemistry. XXI. Synthetic approaches to cyanopyrroles. Can J Chem. 1980;58:409-411.

European Office Action for Application No. 23186497.6, dated Nov. 20, 2023, 6 pages.

U.S. Appl. No. 15/739,877, filed Dec. 26, 2017, U.S. Pat. No. 10,057,091, Issued.

U.S. Appl. No. 16/739,707, filed Jan. 10, 2020, U.S. Pat. No. 11,066,362, Issued.

U.S. Appl. No. 17/350,013, filed Jun. 17, 2021, U.S. Pat. No. 11,649,206, Issued.

METHOD FOR PRODUCING PYRROLE COMPOUND

CROSS REFERENCE TO RELATED APPLICATION

This present application is a divisional application of U.S. application Ser. No. 17/350,013, filed Jun. 17, 2021, which, in turn, is a divisional application of the U.S. application Ser. No. 16/739,707 filed Jan. 10, 2020, which is a divisional application of the U.S. application Ser. No. 15/739,877 filed Dec. 26, 2017 which is a U.S. National Stage Entry of the International Application No. PCT/JP2016/069258, filed on Jun. 29, 2016, which claims the benefit of priority of the Japanese Patent Application No. 2015-131610 filed Jun. 30, 2015. The entire contents of those applications are incorporated herein for all purposes by this reference.

TECHNICAL FIELD

The present invention relates to a production method of a 3-cyanopyrrole compound possibly useful as an intermediate for pharmaceutical products, a production method of an intermediate for producing a 3-cyanopyrrole compound, and a production method of a pyrrole compound possibly useful as a pharmaceutical product.

BACKGROUND OF THE INVENTION

A pyrrole compound having a substituted sulfonyl group at the 1-position (hereinafter to be referred to as a sulfonylpyrrole compound) may be useful as an acid secretion inhibitor (proton pump inhibitor), a therapeutic drug for a neoplastic disease or an autoimmune disease.

A 3-cyanopyrrole compound is used as an intermediate for producing a sulfonylpyrrole compound. Patent document 1 describes the following method as a production method of a 3-cyanopyrrole compound.

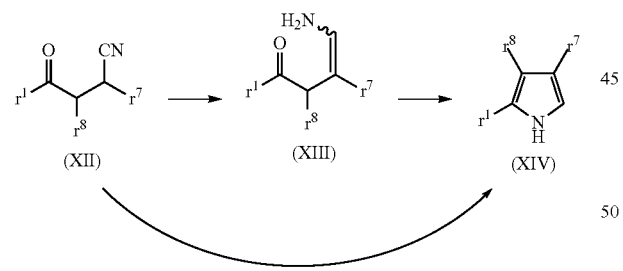

wherein $r^1$ is an optionally substituted hydrocarbon group or an optionally substituted heterocyclic group, $r^7$ is a cyano group or a substituted carboxyl group, and $r^8$ is a hydrogen atom, an optionally substituted hydrocarbon group, an optionally substituted heterocyclic group, a chlorine atom or a fluorine atom.

Patent document 1 discloses that the reduction reaction used to obtain compound (XIII) from compound (XII) can be performed by catalytic hydrogenation in the presence of a hydrogen source and a metal catalyst.

However, this method is not industrially advantageous since it requires a filtration operation to remove metal catalyst after the reaction and the operation is complicated.

DOCUMENT LIST

Patent Document patent document 1: WO2010/098351

SUMMARY OF THE INVENTION

Problems to be Solved by the Invention

An efficient production method of a 3-cyanopyrrole compound possibly useful as an intermediate for pharmaceutical products has been desired.

Means of Solving the Problems

The present inventors have conducted intensive studies in an attempt to solve the aforementioned problems. As a result, they have found a method capable of producing a 3-cyanopyrrole compound in a high yield and superior in operability by performing, in a production method of a 3-cyanopyrrole compound, a reduction reaction in a fixed bed reactor filled with a supported metal catalyst and by a method including continuous hydrogenation, which resulted in the completion of the present invention.

That is, the present invention relates to the following.

[1] A method for producing a compound represented by the formula

wherein $R^1$ is an optionally substituted hydrocarbon group or an optionally substituted heterocyclic group, and $R^2$ is a hydrogen atom, an optionally substituted hydrocarbon group, an optionally substituted heterocyclic group, a chlorine atom or a fluorine atom, or a salt thereof, comprising subjecting a compound represented by the formula

wherein each symbol is as defined above, or a salt thereof to a reduction reaction, wherein the reduction reaction is a continuous hydrogenation in a fixed bed reactor filled with a supported metal catalyst.

[2] A method for producing a compound represented by the formula

wherein R¹ is an optionally substituted hydrocarbon group or an optionally substituted heterocyclic group, and R² is a hydrogen atom, an optionally substituted hydrocarbon group, an optionally substituted heterocyclic group, a chlorine atom or a fluorine atom, or a salt thereof, comprising subjecting a compound represented by the formula

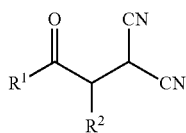
(I)

wherein each symbol is as defined above, or a salt thereof to a reduction reaction, and then to a cyclization reaction, wherein the reduction reaction is a continuous hydrogenation in a fixed bed reactor filled with a supported metal catalyst.

[3] A method for producing a compound represented by the formula

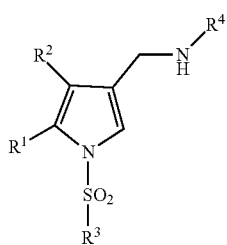
(VIII)

wherein R¹ is an optionally substituted hydrocarbon group or an optionally substituted heterocyclic group, R² is a hydrogen atom, an optionally substituted hydrocarbon group, an optionally substituted heterocyclic group, a chlorine atom or a fluorine atom, R³ is an optionally substituted hydrocarbon group or an optionally substituted heterocyclic group, and R⁴ is an alkyl group, or a salt thereof, comprising (1) subjecting a compound represented by the formula

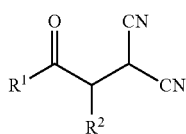
(I)

wherein each symbol is as defined above, or a salt thereof to a reduction reaction, and then to a cyclization reaction to give a compound represented by the formula

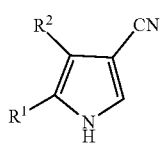
(III)

wherein each symbol is as defined above, or a salt thereof, wherein the reduction reaction is a continuous hydrogenation in a fixed bed reactor filled with a supported metal catalyst, (2) subjecting the obtained compound to a reduction reaction, and then to hydrolysis to give a compound represented by the formula

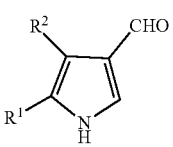
(IV)

wherein each symbol is as defined above, or a salt thereof, (3) reacting the obtained compound with a compound represented by the formula

R³—SO₂—X (V)

wherein R³ is as defined above, and X is a leaving group, or a salt thereof to give a compound represented by the formula

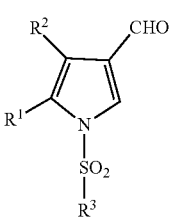
(VI)

wherein each symbol is as defined above, or a salt thereof, and (4) reacting the obtained compound with a compound represented by the formula

R⁴—NH₂ (VII)

wherein R⁴ is as defined above, or a salt thereof.

[4] The production method of any one of the aforementioned [1] to [3] wherein the supported metal catalyst comprises a metal selected from the group consisting of iron (Fe), nickel (Ni), palladium (Pd), platinum (Pt), rhodium (Rh), iridium (Ir), ruthenium (Ru), cobalt (Co), and a combination thereof.

[5] The production method of any one of the aforementioned [1] to [3] wherein the supported metal catalyst comprises palladium (Pd) as a metal.

[6] The production method of any one of the aforementioned [1] to [5] wherein the supported metal catalyst has a metal content of 0.1-15 wt % relative to the whole weight of the supported metal catalyst.

[7] The production method of any one of the aforementioned [1] to [6] wherein the metal of the supported metal catalyst is supported by a carrier selected from the group consisting of carbon, alumina, silica, silica-alumina, zirconia, titania, zeolite, calcium carbonate, calcium carbonate-lead, molecular sieve and polymer.

[8] The production method of any one of the aforementioned [1] to [7] wherein the metal of the supported metal catalyst is supported by alumina as a carrier.

[9] The production method of any one of the aforementioned [1] to [8] wherein the hydrogenation is performed in a solvent containing an acid.

[10] The production method of the aforementioned [9] wherein the acid is acetic acid.

[11] The production method of the aforementioned [9] or [10] wherein the acid is mixed in a proportion of 0.1-50 molar equivalents relative to the compound represented by the formula (I) or a salt thereof.

[12] The production method of any one of the aforementioned [9] to [11] wherein the solvent is selected from tetrahydrofuran and acetonitrile.

[13] The production method of any one of the aforementioned [1] to [12] wherein the hydrogenation is performed at 40-100° C.

[14] The production method of any one of the aforementioned [1] to [13] wherein the hydrogenation is performed under a pressure of 0.01-1 MPa.

[15] The production method of any one of the aforementioned [1] to [14] wherein the compound represented by the formula (I) or a salt thereof is supplied into the fixed bed reactor at WHSV (weight hourly space velocity) of 0.01-1 h$^{-1}$.

[16] The production method of any one of the aforementioned [1] to [15] wherein the compound represented by the formula (I) or a salt thereof is supplied into the fixed bed reactor at a concentration of 1-20 wt % in a solution.

[17] The production method of any one of the aforementioned [1] to [16] wherein the fixed bed reactor is a trickle bed reactor.

[18] A method for producing a compound represented by the formula

wherein R$^1$ is an optionally substituted hydrocarbon group or an optionally substituted heterocyclic group, and R$^2$ is a hydrogen atom, an optionally substituted hydrocarbon group, an optionally substituted heterocyclic group, a chlorine atom or a fluorine atom, or a salt thereof, comprising subjecting a compound represented by the formula

wherein each symbol is as defined above, or a salt thereof to a reduction reaction, and then to hydrolysis, wherein the reduction reaction is a continuous hydrogenation in a fixed bed reactor filled with a supported metal catalyst.

[19] A method for producing a compound represented by the formula

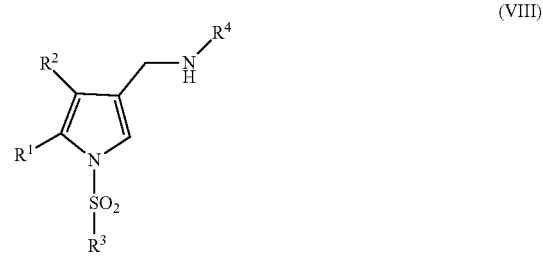

wherein R$^1$ is an optionally substituted hydrocarbon group or an optionally substituted heterocyclic group, R$^2$ is a hydrogen atom, an optionally substituted hydrocarbon group, an optionally substituted heterocyclic group, a chlorine atom or a fluorine atom, R$^3$ is an optionally substituted hydrocarbon group or an optionally substituted heterocyclic group, and R$^4$ is an alkyl group, or a salt thereof, comprising (1) subjecting a compound represented by the formula

wherein each symbol is as defined above, or a salt thereof to a reduction reaction, and then to hydrolysis to give a compound represented by the formula

wherein each symbol is as defined above, or a salt thereof, wherein the reduction reaction is a continuous hydrogenation in a fixed bed reactor filled with a supported metal catalyst, (2) reacting the obtained compound with a compound represented by the formula $$R^3{-}SO_2{-}X \qquad (V)$$

wherein R$^3$ is as defined above, and X is a leaving group, or a salt thereof to give a compound represented by the formula

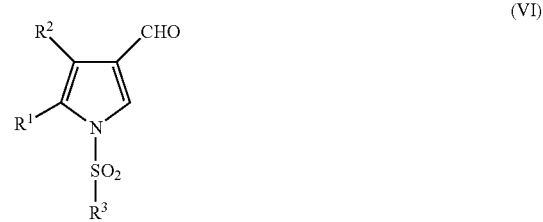

wherein each symbol is as defined above, or a salt thereof, and (3) reacting the obtained compound with a compound represented by the formula

 (VII)

wherein R⁴ is as defined above, or a salt thereof.

[20] The production method of the aforementioned [18] or [19] wherein the supported metal catalyst comprises a metal selected from the group consisting of molybdenum (Mo), nickel (Ni), palladium (Pd), platinum (Pt), chromium (Cr), tungsten (W) and a combination thereof.

[21] The production method of any one of the aforementioned [18] to [20] wherein the supported metal catalyst has a metal content of 0.1-15 wt % relative to the whole weight of the supported metal catalyst.

[22] The production method of any one of the aforementioned [18] to [21] wherein the metal of the supported metal catalyst is supported by zeolite as a carrier.

[23] The production method of the aforementioned [22] wherein the zeolite is HY zeolite.

[24] The production method of any one of the aforementioned [18] to [23] wherein the hydrogenation is performed in a solvent containing an acid.

[25] The production method of the aforementioned [24] wherein the acid is propionic acid.

[26] The production method of the aforementioned [24] or [25] wherein the acid is mixed in a proportion of 0.1-50 molar equivalents relative to the compound represented by the formula (III) or a salt thereof.

[27] The production method of any one of the aforementioned [24] to [26] wherein the solvent is a mixed solvent of water and tetrahydrofuran.

[28] The production method of any one of the aforementioned [18] to [27] wherein the hydrogenation is performed at 40-100° C.

[29] The production method of any one of the aforementioned [18] to [28] wherein the hydrogenation is performed under a pressure of 0.01-1 MPa.

[30] The production method of any one of the aforementioned [18] to [29] wherein the hydrogenation is performed at a hydrogen concentration of 1-15 vol %.

[31] The production method of any one of the aforementioned [18] to [30] wherein the compound represented by the formula (III) or a salt thereof is supplied into the fixed bed reactor at WHSV (weight hourly space velocity) of 0.01-1 h⁻¹.

[32] The production method of any one of the aforementioned [18] to [31] wherein the compound represented by the formula (III) or a salt thereof is supplied into the fixed bed reactor at a concentration of 1-20 wt % in a solution.

[33] The production method of any one of the aforementioned [18] to [32] wherein the fixed bed reactor is a trickle bed reactor.

[34] A method for producing a compound represented by the formula

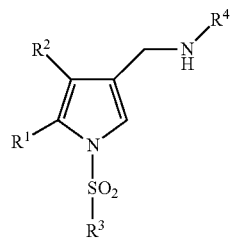 (VIII)

wherein R¹ is an optionally substituted hydrocarbon group or an optionally substituted heterocyclic group, R² is a hydrogen atom, an optionally substituted hydrocarbon group, an optionally substituted heterocyclic group, a chlorine atom or a fluorine atom, R³ is an optionally substituted hydrocarbon group or an optionally substituted heterocyclic group, and R⁴ is an alkyl group, or a salt thereof, comprising (1) subjecting a compound represented by the formula

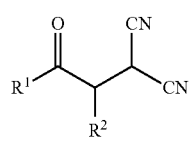 (I)

wherein each symbol is as defined above, or a salt thereof to a reduction reaction, and then to a cyclization reaction to give a compound represented by the formula

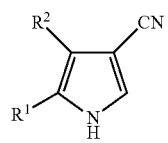 (III)

wherein each symbol is as defined above, or a salt thereof, wherein the reduction reaction is a continuous hydrogenation in a fixed bed reactor filled with a supported metal catalyst (A), (2) subjecting the obtained compound to a reduction reaction and then to hydrolysis to give a compound represented by the formula

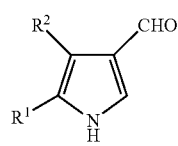 (IV)

wherein each symbol is as defined above, or a salt thereof, wherein the reduction reaction is a continuous hydrogenation in a fixed bed reactor filled with a supported metal catalyst (B), (3) reacting the obtained compound with a compound represented by the formula

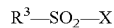 (V)

wherein $R^3$ is as defined above, and X is a leaving group, or a salt thereof to give a compound represented by the formula

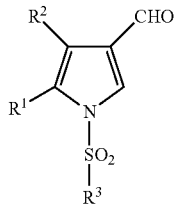

(VI)

wherein each symbol is as defined above, or a salt thereof, and (4) reacting the obtained compound with a compound represented by the formula $$R^4-NH_2 \quad (VII)$$

wherein $R^4$ is as defined above, or a salt thereof.

Effect of the Invention

According to the method of the present invention, the yield may be improved as compared to the conventional batch methods. In addition, the amount of the catalyst can be reduced, and the method is advantageous because a filtration operation to remove the catalyst is not necessary and the safety and operability can be improved.

According to the method of the present invention, moreover, lowering of catalyst activity due to continuous use of a supported metal catalyst may be less, and the catalyst can be continuously used for a long term. Occurrence of a side reaction can be suppressed to the minimum, and the production steps can also be advantageously controlled precisely. The amount of the catalyst to be used can be decreased, the amount of the solvent to be used can be decreased since filtration and washing operation are not necessary, and an economically advantageous production method with less environmental load and suitable for industrial production can be obtained.

DETAILED DESCRIPTION OF THE INVENTION

Figure 1:
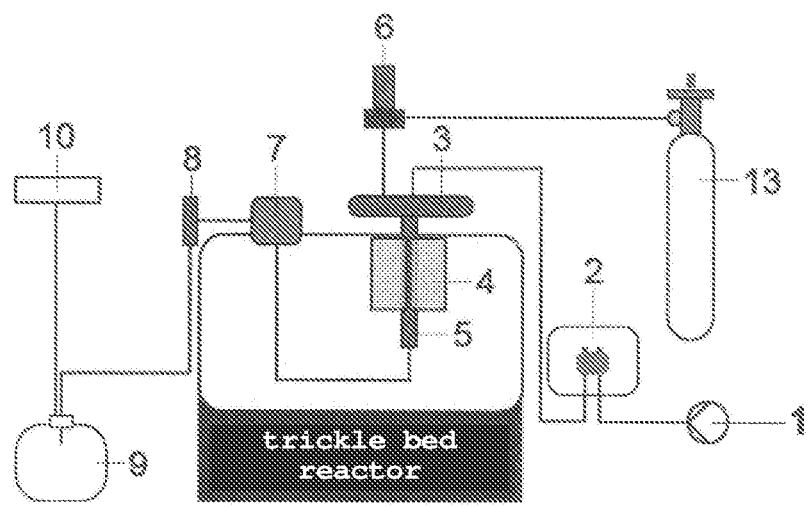
FIG. 1 is a schematic figure showing one embodiment of a reaction apparatus to be used in the production method of the present invention.

In the present specification, a compound represented by the formula (I) is sometimes abbreviated as "compound (I)". The same applies to compounds represented by other formulas.

The definition of each symbol in the formula is explained in detail in the following.

Examples of the "hydrocarbon group" of the "optionally substituted hydrocarbon group" for $R^1$ include a chain or cyclic hydrocarbon group (e.g., alkyl, alkenyl, alkynyl, cycloalkyl, aryl, aralkyl etc.). Of these, a chain or cyclic hydrocarbon group having a carbon number of 1 to 16 and the like are preferable.

Examples of the "alkyl" include $C_{1-6}$ alkyl (e.g., methyl, ethyl, propyl, isopropyl, butyl, isobutyl, sec-butyl, tert-butyl, pentyl, hexyl etc.) and the like.

Examples of the "alkenyl" include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like.

Examples of the "alkynyl" include $C_{2-6}$ alkynyl (e.g., ethynyl, propargyl, 1-butynyl, 2-butynyl, 3-butynyl, 1-hexynyl etc.) and the like.

Examples of the "cycloalkyl" include $C_{3-7}$ cycloalkyl (e.g., cyclopropyl, cyclobutyl, cyclopentyl, cyclohexyl, cycloheptyl etc.) and the like.

Examples of the "aryl" include $C_{6-14}$ aryl (e.g., phenyl, 1-naphthyl, 2-naphthyl, 2-biphenylyl, 3-biphenylyl, 4-biphenylyl, 2-anthryl etc.) and the like.

Examples of the "aralkyl" include $C_{7-16}$ aralkyl (e.g., phenyl-$C_{1-6}$ alkyl, naphthyl-$C_{1-6}$ alkyl, diphenyl-$C_{1-4}$ alkyl etc. such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like) and the like.

When the above-mentioned hydrocarbon group is alkyl, alkenyl or alkynyl, it is optionally substituted by 1 to 3 substituents selected from (1) a halogen atom (e.g., a fluorine atom, a chlorine atom, a bromine atom, an iodine atom etc.), (2) nitro, (3) cyano, (4) hydroxy, (5) $C_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., a fluorine atom, a chlorine atom, a bromine atom, an iodine atom), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., fluorine atom, chlorine atom, bromine atom, iodine atom), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino (e.g., pyrrolidin-1-yl, piperidino, piperazin-1-yl, morpholino, thiomorpholino, hexahydroazepin-1-yl etc.) optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) containing, besides carbon atom, 1 or 2 kinds of 1 to 4 hetero atoms selected from a nitrogen atom, a sulfur atom and an oxygen atom, (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), and the like.

In addition, when the above-mentioned hydrocarbon group is cycloalkyl, aryl or aralkyl, it is optionally substituted by 1 to 5 (preferably 1 to 3) substituents selected from (1) a halogen atom (e.g., a fluorine atom, a chlorine atom, a bromine atom, an iodine atom etc.), (2) nitro, (3) cyano, (4) hydroxy, (5) $C_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., a fluorine atom, a chlorine atom, a bromine atom, an iodine atom), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., fluorine atom, chlorine atom, bromine atom, iodine atom), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl, trifluoromethylsulfonyl etc.) optionally having 1 to 3 halogen atoms (e.g., a fluorine atom, a chlorine atom, a bromine atom, an iodine atom), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino (e.g., pyrrolidin-1-yl, piperidino, piperazin-1-yl, morpholino, thiomorpholino, hexahydroazepin-1-yl etc.) optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) containing, besides carbon atom, 1 or 2 kinds of 1 to 4 hetero atoms selected from a nitrogen atom, a sulfur atom and an oxygen atom, (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) a $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., fluorine atom, chlorine atom, bromine atom, iodine atom) or hydroxy group(s), (51) a $C_{2-6}$ alkenyl group (e.g., allyl, isopropenyl, isobutenyl, 1-methylallyl, 2-pentenyl, 2-hexenyl etc.) optionally having 1 to 3 halogen atoms (e.g., fluorine atom, chlorine atom, bromine atom, iodine atom), (52) a $C_{2-6}$ alkynyl group (e.g., propargyl, 2-butynyl, 3-butynyl, 3-pentynyl, 3-hexynyl etc.), (53) mono-$C_{3-7}$ cycloalkyl-carbamoyl (e.g., cyclopropylcarbamoyl, cyclobutylcarbamoyl etc.), and (54) 5- to 10-membered heterocyclyl-carbonyl containing, besides carbon atom, 1 or 2 kinds of 1 to 4 hetero atoms selected from a nitrogen atom, a sulfur atom and an oxygen atom (e.g., 4-morpholinocarbonyl etc.) and the like.

Examples of the "heterocyclic group" of the "optionally substituted heterocyclic group" for $R^1$ include a 3- to 8-membered heterocyclic group (preferably a 5- or 6-membered heterocyclic group) containing 1 to 4 hetero atoms such as a nitrogen atom (optionally oxidized), an oxygen atom, a sulfur atom (optionally mono- or dioxidized) and the like, or a group formed by condensing a 3- to 8-membered heterocyclic group (preferably a 5- or 6-membered heterocyclic group) containing 1 to 4 hetero atoms such as a nitrogen atom (optionally oxidized), an oxygen atom, a sulfur atom (optionally mono- or dioxidized) and the like, with a benzene ring or a 3- to 8-membered heterocyclic group (preferably 5- or 6-membered heterocyclic group) containing 1 to 4 hetero atoms such as a nitrogen atom (optionally oxidized), an oxygen atom, a sulfur atom (optionally mono- or dioxidized) and the like, preferably a group formed by condensing the 5- or 6-membered heterocyclic group with a 5- or 6-membered ring containing 1 to 4 hetero atoms such as a nitrogen atom (optionally oxidized), an oxygen atom, a sulfur atom (optionally mono- or dioxidized) and the like.

Specifically, aziridinyl (e.g., 1- or 2-aziridinyl), azirinyl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazole-1-, 4- or 5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), thiazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein nitrogen atom is oxidized (e.g., 2-, 3- or 4-pyridyl-N-oxide), pyridazinyl (e.g., 3- or 4-pyridazinyl), pyridazinyl wherein one or both of nitrogen atoms is/are oxidized (e.g., 3-, 4-, 5- or 6-pyridazinyl-N-oxide), pyrimidinyl (e.g., 2-, 4- or 5-pyrimidinyl), pyrimidinyl wherein one or both of nitrogen atoms is/are oxidized (e.g., 2-, 4-, 5- or 6-pyrimidinyl-N-oxide), pyrazinyl, piperidinyl (e.g., 1-, 2-, 3- or 4-piperidinyl), piperazinyl (e.g., 1- or 2-piperazinyl), indolyl (e.g., 3H-indol-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3-, 4-, 5-, 6-, 7- or 8-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromen-2- or 3-yl), 2-benzo[b]thienyl, 3-benzo[b]thienyl, 2-benzo[b]furanyl, 3-benzo[b]furanyl, 2,3-dihydro-1-benzofuranyl, 2,1,3-benzothiadiazolyl, 2,3-dihydro-1,4-benzodioxin-5- or -6-yl, 1,3-benzothiazol-6-yl, 1,1-dioxide-2,3-dihydro-1-benzothien-6-yl, 1-benzothienyl and the like are used.

Examples of the "substituent" of the heterocyclic group include those similar to the substituents optionally present when the "hydrocarbon group" for the above-mentioned $R^1$ is cycloalkyl, aryl or aralkyl. The number of the substituents is 1 to 5, preferably 1 to 3.

Examples of the "optionally substituted hydrocarbon group" for $R^2$ include groups similar to the "optionally substituted hydrocarbon group" for the aforementioned $R^1$.

Examples of the "optionally substituted heterocyclic group" for $R^2$ include groups similar to the "optionally substituted heterocyclic group" for the aforementioned $R^1$.

Examples of the "optionally substituted hydrocarbon group" for $R^3$ include groups similar to the "optionally substituted hydrocarbon group" for the aforementioned $R^1$.

Examples of the "optionally substituted heterocyclic group" for $R^3$ include groups similar to the "optionally substituted heterocyclic group" for the aforementioned $R^1$.

Examples of the "leaving group" for X include halogen atoms such as chlorine, bromine and the like, a hydroxy group, a methanesulfonyloxy group, a trifluoromethanesulfonyloxy group, a benzenesulfonyloxy group, a p-toluenesulfonyloxy group, a p-nitrobenzenesulfonyloxy group, an o-nitrobenzenesulfonyloxy group and the like.

Examples of the "alkyl group" for $R^4$ include $C_{1-4}$ alkyl groups such as methyl, ethyl, propyl, isopropyl, butyl, isobutyl, sec-butyl, tert-butyl etc. and the like.

As $R^3$, a "nitrogen-containing monocyclic heterocyclic group optionally condensed with a benzene ring or a heterocycle (as the heterocyclic group, groups similar to the heterocyclic group of the "optionally substituted heterocyclic group" for the aforementioned $R^1$ can be mentioned)" (e.g., 5- or 6-membered aromatic nitrogen-containing monocyclic heterocyclic groups such as thiazolyl, imidazolyl, pyrazolyl, pyridyl, pyrimidinyl, pyridazinyl, pyrazinyl and the like, and the like) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) oxo and (viii) $C_{1-6}$ alkoxy-carbonyl (e.g., methoxycarbonyl, ethoxycarbonyl, propoxycarbonyl, tert-butoxycarbonyl etc.) is preferable.

As $R^3$, particularly, a 6-membered nitrogen-containing aromatic heterocyclic group (e.g., pyridyl groups (e.g., 2-, 3- or 4-pyridyl etc.), pyrimidinyl groups (e.g., 2-, 4- or 5-pyrimidinyl etc.), pyridazinyl groups (e.g., 3- or 4-pyridazinyl etc.) etc.) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (vi) an amino group optionally substituted by $C_{1-6}$ alkyl (e.g., methyl, ethyl, propyl, isopropyl, butyl, isobutyl, sec-butyl, tert-butyl, pentyl, hexyl etc.) is preferable, and a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) is further preferable. As $R^3$, a pyridyl group is particularly preferable.

As $R^1$, [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) a $C_{1-6}$ alkyl group substituted by 1 to 3 hydroxy (e.g., hydroxymethyl, hydroxyethyl etc.), (ix) $C_{1-6}$ alkylthio (e.g., methylthio, ethylthio, propylthio, isopropylthio, butylthio, isobutylthio, sec-butylthio, pentylthio, hexylthio etc.) optionally substituted by 1 to 5 (preferably 1 to 3) halogens (e.g., fluorine, chlorine, bromine, iodine) and (x) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acyl (e.g., acetyl), (vi) nitro and (vii) amino is preferable.

Of these, as $R^1$, [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl,

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acyl (e.g., acetyl), (vi) nitro and (vii) amino is preferable.

Particularly, [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) is preferable.

Of those mentioned above, a preferable embodiment of $R^1$ include [1] a phenyl group optionally substituted by 1 to 5 substituents selected from (i) a halogen atom and (ii) $C_{1-6}$ alkyl optionally substituted by 1 to 5 halogen atoms, [2] a pyridyl group optionally substituted by 1 to 4 substituents selected from lower ($C_{1-6}$) alkyl, a halogen atom, alkoxy ($C_{1-6}$ alkoxy), cyano, acyl (e.g., acetyl), nitro and amino, and the like.

As $R^1$, a phenyl group, a 2-fluorophenyl group, a 2-methylphenyl group, a 2-fluoropyridin-3-yl group, a 3-fluoropyridin-4-yl group, a 2-chloropyridin-3-yl group, a 6-chloropyridin-3-yl group, a 4-methylpyridin-3-yl group, a 2-methylpyridin-3-yl group, a 3-methylpyridin-2-yl group, a 2-trifluoromethylpyridin-3-yl group and a 6'-chloro-2,3'-bipyridin-5-yl group are particularly preferable.

Preferably, $R^2$ is a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a fluorine atom or a chlorine atom, and a hydrogen atom is particularly preferable.

As $R^4$, methyl or ethyl is preferable, and methyl is particularly preferable.

The above-mentioned preferable embodiments of the substituents for $R^1$ to $R^4$ may be optionally combined to achieve a preferable embodiment.

In a preferable embodiment, for example, $R^1$ is [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) a $C_{1-6}$ alkyl group substituted by 1 to 3 hydroxy (e.g., hydroxymethyl, hydroxyethyl etc.), (ix) $C_{1-6}$ alkylthio (e.g., methylthio, ethylthio, propylthio, isopropylthio, butylthio, isobutylthio, sec-butylthio, pentylthio, hexylthio etc.) optionally substituted by 1 to 5 (preferably 1 to 3) halogens (e.g., fluorine, chlorine, bromine, iodine) and (x) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl,

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acyl (e.g., acetyl), (vi) nitro and (vii) amino, or

[4] a bipyridyl group optionally substituted by 1 to 3 halogen atoms (e.g., fluorine, chlorine, bromine, iodine);

$R^2$ is a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a fluorine atom or a chlorine atom, $R^3$ is a 5- or 6-membered aromatic nitrogen-containing monocyclic heterocyclic group (e.g., thiazolyl, imidazolyl, pyrazolyl, pyridyl, pyrimidinyl, pyridazinyl, pyrazinyl and the like) or an imidazo[1,2-a]pyrimidinyl group, which are optionally substituted 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.) and (vii) $C_{1-6}$ alkoxy-carbonyl (e.g., methoxycarbonyl, ethoxycarbonyl, propoxycarbonyl, tert-butoxycarbonyl etc.); and $R^4$ is methyl or ethyl.

In the formulas (I), (II), (III) and (IV), a combination of the above-mentioned $R^1$ and $R^2$ is preferable. In the formula (VI), a combination of the above-mentioned $R^1$, $R^2$ and $R^3$ is preferable.

In a more preferable embodiment, $R^1$ is [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), and $R^2$ is a hydrogen atom or a fluorine atom, $R^3$ is a pyridyl group optionally substituted 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), and $R^4$ is methyl.

In the formulas (I), (II), (III) and (IV), a combination of the above-mentioned $R^1$ and $R^2$ is more preferable. In the formula (VI), a combination of the above-mentioned $R^1$, $R^2$ and $R^3$ is more preferable.

In a particularly preferable embodiment,

R¹ is a phenyl group optionally substituted by 1 to 5 (preferably 1 to 3) substituents selected from (i) a halogen atom and (ii) $C_{1-6}$ alkyl optionally substituted by 1 to 5 (preferably 1 to 3) halogens, R² is a hydrogen atom or a fluorine atom, R³ is a pyridyl group optionally substituted by 1 to 3 substituents selected from (i) $C_{1-6}$ alkyl optionally substituted by 1 to 5 (preferably 1 to 3) halogens and (ii) $C_{1-6}$ alkoxy optionally substituted by 1 to 5 (preferably 1 to 3) halogens, and R⁴ is methyl.

In the formulas (I), (II), (III) and (IV), a combination of the above-mentioned R¹ and R² is particularly preferable. In the formula (VI), a combination of the above-mentioned R¹, R² and R³ is particularly preferable.

As the leaving group for X, a halogen atom such as chlorine, bromine or the like or a hydroxy group is preferable, and a halogen atom is more preferable.

Preferable examples of compound (II) include 4-(2-fluorophenyl)-2-(iminomethyl)-4-oxobutanenitrile or a salt thereof and the like.

Preferable examples of compound (III) include 5-(2-fluorophenyl)-1H-pyrrole-3-carbonitrile or a salt thereof and the like.

Preferable examples of compound (IV) include 5-(2-fluorophenyl)-1H-pyrrole-3-carbaldehyde or a salt thereof and the like.

Preferable examples of compound (VI) include 5-(2-fluorophenyl)-1-(pyridin-3-ylsulfonyl)-1H-pyrrole-3-carbaldehyde or a salt thereof and the like.

Preferable examples of compound (VIII), which is the object compound, include

1-{5-(2-fluorophenyl)-1-[(6-methylpyridin-3-yl)sulfonyl]-1H-pyrrol-3-yl}-N-methylmethanamine or a salt thereof, 1-[4-fluoro-5-phenyl-1-(pyridin-3-ylsulfonyl)-1H-pyrrol-3-yl]-N-methylmethanamine or a salt thereof, N-methyl-1-[5-(4-methyl-3-thienyl)-1-(pyridin-3-ylsulfonyl)-1H-pyrrol-3-yl]methanamine or a salt thereof, 1-[5-(2-fluoropyridin-3-yl)-1-(pyridin-3-ylsulfonyl)-1H-pyrrol-3-yl]-N-methylmethanamine or a salt thereof, 1-[5-(2-fluorophenyl)-1-(pyridin-3-ylsulfonyl)-1H-pyrrol-3-yl]-N-methylmethanamine or a salt thereof, N-methyl-1-[5-(2-methylphenyl)-1-(pyridin-3-ylsulfonyl)-1H-pyrrol-3-yl]methanamine or a salt thereof, 1-{4-fluoro-5-(2-fluoropyridin-3-yl)-1-[(4-methylpyridin-2-yl)sulfonyl]-1H-pyrrol-3-yl}-N-methylmethanamine or a salt thereof, and the like.

The object compound, a compound represented by the formula (VIII) or a salt thereof, may have a highly strong proton pump inhibitory action, and may be useful as an acid secretion inhibitor (proton pump inhibitor); an agent clinically useful for the prophylaxis or treatment of peptic ulcer (e.g., gastric ulcer, duodenal ulcer, anastomotic ulcer, ulcer caused by non-steroidal anti-inflammatory agents, ulcer due to postoperative stress etc.), Zollinger-Ellison syndrome, gastritis, erosive esophagitis, reflux esophagitis, symptomatic gastroesophageal reflux disease (symptomatic GERD), Barrett esophagus, functional dyspepsia, gastric cancer, stomach MALT lymphoma, or gastric hyperacidity; or an inhibitor of upper gastrointestinal hemorrhage due to peptic ulcer, acute stress ulcer, hemorrhagic gastritis or invasive stress or recurrence of ulcer due to non-steroidal anti-inflammatory agents and the like.

The production method of the present invention is explained in detail in the following.

As salts of compounds (I)-(VIII) in reaction schemes, metal salt, ammonium salt, salts with organic bases, salts with inorganic bases, salts with organic acids, salts with basic or acidic amino acids and the like can be mentioned. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysine, ornithine and the like. Preferable examples of the salt with acidic amino acid include a salt with aspartic acid, glutamic acid and the like.

While the compounds obtained in respective steps can be used for the next reaction in the form of a reaction mixture or a crude product, they can also be isolated from the reaction mixture by conventional means, and easily purified by separation means such as recrystallization, distillation, chromatography and the like.

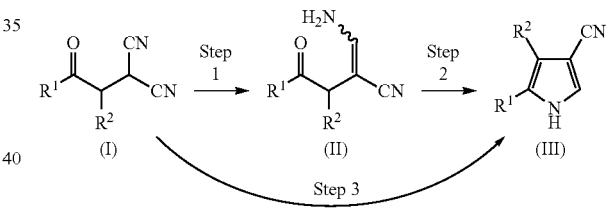

Step 1

Compound (II) or a salt thereof can be produced by continuous hydrogenation of compound (I) or a salt thereof dissolved in a solvent in a fixed bed reactor filled with a supported metal catalyst (hereinafter supported metal catalyst used in step 1 or 3 is to be referred to as supported metal catalyst (A)).

The supported metal catalyst means a catalyst in which the catalyst metal is supported by a carrier.

The metal of the supported metal catalyst (A) is selected from the group consisting of iron (Fe), nickel (Ni), palladium (Pd), platinum (Pt), rhodium (Rh), iridium (Ir), ruthenium (Ru), cobalt (Co), and a combination thereof, and a carrier to support these metals is selected from the group consisting of carbon, alumina, silica, silica-alumina, zirconia, titania, zeolite, calcium carbonate, calcium carbonate-lead, molecular sieve and polymer (e.g., polysilane; urea resin; polystyrene; phenol resin; polypropylene; cellulose; polyurethane; polyamide; polyester; polyethylene; polymethylpentene; polybutene; polybutadiene; polyisobutylene; fluorine resin such as polytetrafluoroethylene and the like; natural rubber; styrene-butadiene rubber; butyl rubber etc.). Of these, a palladium alumina catalyst is preferable. The content of the metal in the supported metal catalyst (A) is 0.1 to 15 wt %, preferably 0.5 to 5 wt %, of the whole weight of the supported metal catalyst (A).

The solvent to be used for continuous hydrogenation is not particularly limited as long as the reaction proceeds and, for example, alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), nitriles (e.g., acetonitrile and the like), carboxylic acids (e.g., acetic acid and the like), water or a mixture thereof can be mentioned, with preference given to tetrahydrofuran or acetonitrile.

An acid (e.g., formic acid, acetic acid, propionic acid, trifluoroacetic acid, citric acid, methanesulfonic acid, benzenesulfonic acid, p-toluenesulfonic acid, trifluoromethanesulfonic acid, hydrochloric acid, sulfuric acid, nitric acid and the like) may be mixed with the solvent. As the acid, acetic acid or propionic acid is preferable, and acetic acid is particularly preferable. An acid in an amount of generally 0.1 to 50 molar equivalents, preferably 0.5 to 15 molar equivalents, relative to compound (I) or a salt thereof may be mixed.

The concentration of compound (I) or a salt thereof dissolved in the solvent is generally 1 to 20 wt %, preferably 3 to 10 wt %.

The reaction temperature is generally 40 to 100° C., preferably 50 to 70° C.

The amount of hydrogen to be supplied to a fixed bed reactor is generally 1 to 10 molar equivalents relative to the supply amount of compound (I) or a salt thereof. The hydrogen pressure at which the reaction is performed is generally 0.01 to 1 MPa, preferably 0.01 to 0.3 MPa.

As the feeding rate of the solution of compound (I) or a salt thereof to a fixed bed reactor, the weight hourly space velocity (WHSV) calculated from the quotient of the supply amount per hour (kg/hr) of compound (I) or a salt thereof and the weight (kg) of supported metal catalyst (A) filled in the fixed bed reactor is generally 0.01 to 1 $h^{-1}$, preferably 0.03 to 0.1 $h^{-1}$.

As the fixed bed reactor, a trickle bed reactor in which a solution of compound (I) or a salt thereof and hydrogen gas are introduced from the upper part of the fixed bed reactor and flowed downward is preferable from the aspects of suppression of abrasion of the catalyst due to the trembling of the catalyst.

Compound (I) or a salt thereof can be produced according to the method described in, for example, JP-A-6-9554 and the like, or a method analogous thereto.

A schematic figure of one embodiment of the reaction apparatus used in Step 1 (continuous hydrogenation) is shown in FIG. 1. In FIG. 1, 1 is a feed solution, 2 is a feed pump, 3 is a gas-liquid mixing zone, 4 is a jacket for heating reactor, 5 is a trickle bed reactor (filled with catalyst), 6 is a mass flow controller, 7 is a chamber, 8 is a pressure regulating valve, 9 is a reaction mixture recovery container, 10 is a hydrogen exhaust device, and 13 is a hydrogen tank.

A solution containing compound (I) or a salt thereof (feed solution) and hydrogen gas are continuously supplied from the upper part of trickle bed reactor 5 filled with supported metal catalyst (A), and flowed downward through the reactor, and compound (I) or a salt thereof and hydrogen are reacted in the presence of a catalyst in the inside of the reactor. The reaction mixture containing the resulting compound (II) or a salt thereof is continuously taken out from the lower part of the trickle bed reactor 5 and recovered in the reaction mixture recovery container 9. The separated hydrogen gas is exhausted from the hydrogen exhaust device 10.

Step 2

Compound (III) or a salt thereof can be produced by cyclizing compound (II) or a salt thereof.

The cyclization reaction is preferably performed under acidic conditions. As the acid to be used, organic carboxylic acid (e.g., formic acid, acetic acid, propionic acid, trifluoroacetic acid, citric acid and the like), organic sulfonic acid (e.g., methanesulfonic acid, benzenesulfonic acid, p-toluenesulfonic acid, trifluoromethanesulfonic acid and the like), inorganic acid (e.g., hydrochloric acid, sulfuric acid, nitric acid and the like) and the like can be mentioned. The amount of the acid to be used is about 0.01 to about 100 molar equivalents, preferably 0.5 to 20 molar equivalents, per 1 mol of compound (II).

The solvent in this reaction is not particularly limited as long as the reaction proceeds and, for example, alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), nitriles (e.g., acetonitrile and the like), carboxylic acids (e.g., acetic acid and the like), water or a mixture thereof can be mentioned, with preference given to tetrahydrofuran or acetonitrile. The amount of the solvent to be used is generally about 1 to about 1000 ml, preferably 3 to 100 ml, per 1 g of compound (II).

The reaction temperature is generally about −10° C. to about 100° C., preferably 30 to 70° C. The reaction pressure is generally 0 to 0.7 MPa. The reaction time is generally about 0.1 to about 48 hr, preferably 0.5 to 6 hr.

Step 3

Compound (III) or a salt thereof can be produced by subjecting compound (II) or a salt thereof obtained in the aforementioned step 1, without isolation, to a continuous cyclization reaction.

Compound (III) or a salt thereof can be produced by separating the hydrogen gas from the reaction mixture obtained in Step 1, and subjecting same to a continuous heating reaction in a continuous reactor (e.g., tubular reactor, fixed bed reactor, continuous stirred-tank reactor and the like). When continuous hydrogenation is performed in a solvent containing acid in Step 1, the cyclization reaction can be performed without adding acid.

The reaction temperature is generally 40 to 100° C., preferably 50 to 70° C. The reaction pressure is generally 0 to 0.7 MPa. The reaction time (residence time in the reactor) is generally about 0.1 to about 48 hr, preferably 0.5 to 6 hr.

Figure 2:
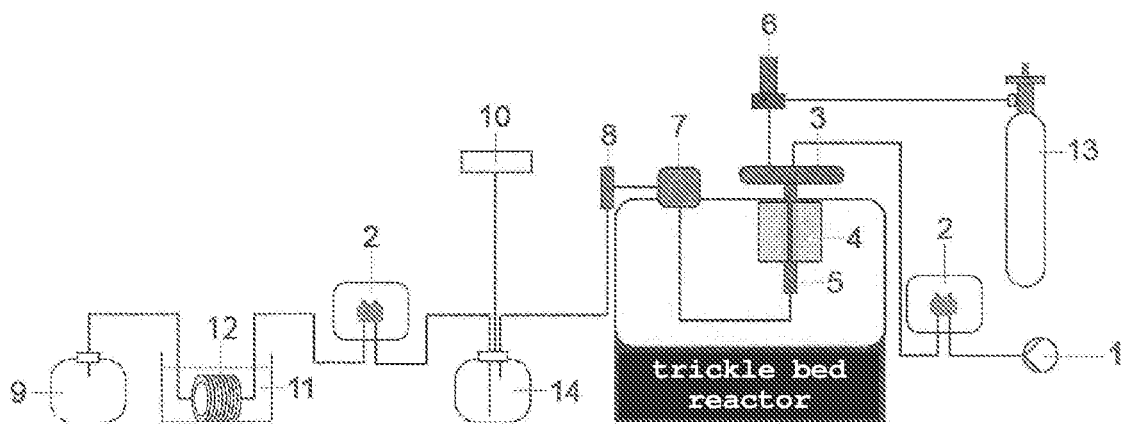
FIG. 2 is a schematic figure showing one embodiment of a reaction apparatus to be used in the production method of the present invention.

A schematic figure of one embodiment of the reaction apparatus used in Step 3 is shown in FIG. 2. In FIG. 2, 1 is a feed solution, 2 is a feed pump, 3 is a gas-liquid mixing zone, 4 is a jacket for heating reactor, 5 is a trickle bed reactor (filled with catalyst), 6 is a mass flow controller, 7 is a chamber, 8 is a pressure regulating valve, 9 is a reaction mixture recovery container, 10 is a hydrogen exhaust device, 11 is a hot-water bath (for regulating reactor temperature), 12 is a tubular reactor, 13 is a hydrogen tank, and 14 is a gas-liquid separator.

A solution containing compound (I) or a salt thereof (feed solution) and hydrogen gas are continuously supplied from the upper part of trickle bed reactor 5 filled with supported metal catalyst (A), and flowed downward through the reactor, and compound (I) or a salt thereof and hydrogen are reacted in the presence of a catalyst in the inside of the reactor. The reaction mixture containing the resulting compound (II) or a salt thereof is continuously taken out from the lower part of the trickle bed reactor 5 and separated into the hydrogen gas and the reaction mixture by the gas-liquid separator 14. The separated hydrogen gas is exhausted from the hydrogen exhaust device 10. The reaction mixture is flowed in the tubular reactor 12 heated in the hot-water bath 11, and the reaction mixture containing the resulting compound (III) or a salt thereof is recovered in the reaction mixture recovery container 9.

Figure 3:
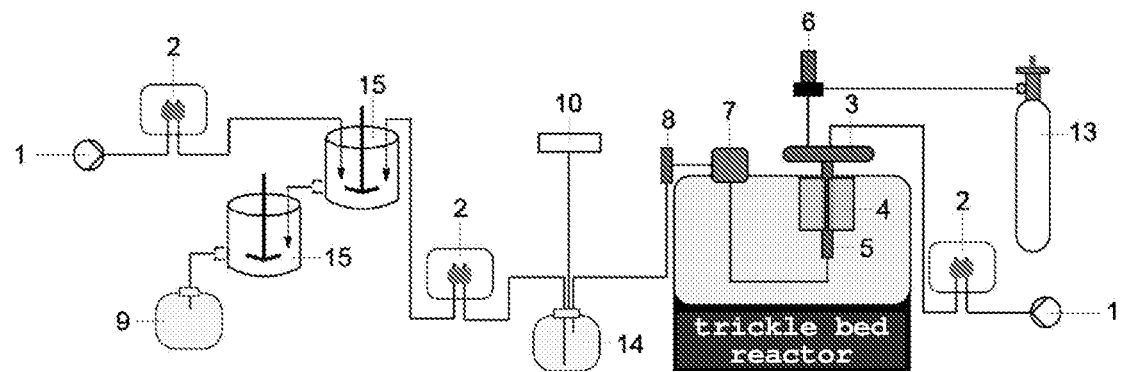
FIG. 3 is a schematic figure showing one embodiment of a reaction apparatus to be used in the production method of the present invention.

A schematic figure of another embodiment of a reaction apparatus used in Step 3 is shown in FIG. 3. In FIG. 3, 1 is a feed solution, 2 is a feed pump, 3 is a gas-liquid mixing zone, 4 is a jacket for heating reactor, 5 is a trickle bed reactor (filled with catalyst), 6 is a mass flow controller, 7 is a chamber, 8 is a pressure regulating valve, 9 is a reaction mixture recovery container, 10 is a hydrogen exhaust device, 13 is a hydrogen tank, 14 is a gas-liquid separator, and 15 is a continuous stirred-tank reactor.

A solution containing compound (I) or a salt thereof (feed solution) and hydrogen gas are continuously supplied from the upper part of trickle bed reactor 5 filled with supported metal catalyst (A), and flowed downward through the reactor, and compound (I) or a salt thereof and hydrogen are reacted in the presence of a catalyst in the inside of the reactor. The reaction mixture containing the resulting compound (II) or a salt thereof is continuously taken out from the lower part of the trickle bed reactor 5 and separated into the hydrogen gas and the reaction mixture by the gas-liquid separator 14. The separated hydrogen gas is exhausted from the hydrogen exhaust device 10. The reaction mixture containing the resulting compound (II) or a salt thereof and a solution containing acid (e.g., mixture of acetic acid and tetrahydrofuran) are continuously supplied to the continuous stirred-tank reactor 15 (two reactors) and reacted with stirring, and the reaction mixture containing the resulting compound (III) or a salt thereof is recovered in the reaction mixture recovery container 9.

A palladium alumina catalyst is preferably used as the supported metal catalyst (A) in the hydrogenation in Step 1 or Step 3 since the conversion rate (conversion rate from compound (I) to compound (III)) and selectivity (ratio of compound (III) in the resultant product) can be improved in two steps of Step 1 and Step 2, or Step 3. The content of palladium in the palladium alumina catalyst is preferably 0.5 to 5 wt %, particularly preferably 0.5 to 2.0 wt %, of the whole weight of the palladium alumina catalyst.

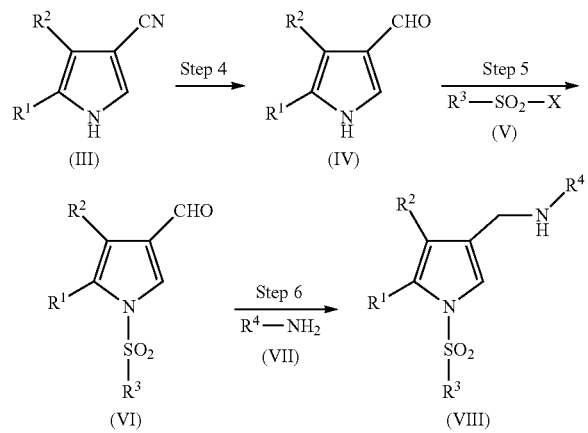

Step 4

Compound (IV) or a salt thereof can be produced by reducing compound (III) or a salt thereof and hydrolyzing the reduced product.

As the reduction reaction, a method using metal hydride and a method using catalytic hydrogenation can be mentioned.

Examples of the metal hydride include boron reagent (e.g., sodium borohydride, lithium borohydride, zinc borohydride, sodium cyanoborohydride, sodium triacetoxyborohydride, lithium cyanoborohydride and the like), aluminum reagent (e.g., diisobutylaluminum hydride, aluminum hydride, lithium aluminum hydride and the like), borane complex (e.g., borane-THF complex, borane-dimethyl sulfide, borane-pyridine and the like), catechol borane and the like. The amount of the metal hydride to be used is, for example, about 0.2 to about 10 mol, preferably about 0.2 to about 5 mol, per 1 mol of compound (III).

The reduction reaction by metal hydride is generally performed in a solvent inert to the reaction. Examples of such solvent include aromatic hydrocarbons (e.g., toluene, xylene, chlorobenzene and the like), aliphatic hydrocarbons (e.g., heptane, hexane and the like), halogenated hydrocarbons (e.g., chloroform, dichloromethane and the like), ethers (e.g., diethyl ether, tetrahydrofuran, dioxane and the like), and a mixture thereof. The amount of the solvent to be used is generally about 1 to about 100 ml, preferably about 1 to about 50 ml, per 1 g of compound (III).

The reaction temperature is generally about −100° C. to about 100° C., preferably about −70° C. to about 50° C. The reaction time is generally about 0.5 to about for 24 hr, preferably about for 0.5 hr to about for 5 hr.

The catalytic hydrogenation can be performed in the presence of a hydrogen source and a metal catalyst. Examples of the metal catalyst include palladium catalyst (e.g., palladium carbon, palladium hydroxide carbon, palladium oxide and the like), nickel catalyst (e.g., Raney-nickel and the like), platinum catalyst (e.g., platinum oxide, platinum carbon and the like), rhodium catalyst (e.g., rhodium carbon and the like) and the like. Of these, palladium carbon or Raney-nickel is preferable. The amount of the metal catalyst to be used is about 0.0001 to about 10 mol, preferably about 0.001 to about 5 mol, per 1 mol of compound (III), or about 0.1 g to about 10 g, preferably about 0.3 g to about 5 g, per 1 g of compound (III).

Examples of the hydrogen source include hydrogen gas, formic acid, ammonium formate, triethylammonium formate, sodium phosphinate, hydrazine and the like. When a hydrogen source other than hydrogen gas is used, a compound of a hydrogen source is used in about 1 to about 100 mol, preferably about 1 to about 50 mol, more preferably about 1 to about 10 mol, for example, about 1 to about 5 mol, per 1 mol of compound (III).

The catalytic hydrogenation is generally performed in a solvent inert to the reaction. Examples of such solvent include alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), carboxylic acids (e.g., acetic acid and the like), water and a mixture thereof. The amount of the solvent to be used is generally about 1 to about 1000 ml, preferably about 1 to about 100 ml, per 1 g of compound (III).

The hydrogen pressure under which the reaction is performed is generally about 0 to about 10 atm, preferably about 0 to about 5 atm. The reaction temperature is generally about −50° C. to about 100° C., preferably about −20° C. to about 50° C. The reaction time is generally about 1 to about 100 hr, preferably about 1 to about 24 hr, for example, about 1 to about 10 hr.

The reduction reaction of Step 4 is preferably a continuous hydrogenation reaction in a fixed bed reactor filled with a supported metal catalyst (hereinafter supported metal catalyst used in Step 4 is referred to as supported metal catalyst (B)).

Compound (IV) or a salt thereof can be produced by continuous hydrogenation of compound (III) or a salt thereof, dissolved in a solvent, in a fixed bed reactor filled with a supported metal catalyst (B).

The metal of the supported metal catalyst (B) is selected from the group consisting of molybdenum (Mo), nickel (Ni), palladium (Pd), platinum (Pt), chromium (Cr), tungsten (W), and a combination thereof, and a carrier to support these metals is selected from the group consisting of carbon, alumina, silica, silica-alumina, zirconia, titania, zeolite (e.g., HY zeolite), calcium carbonate, calcium carbonate-lead, molecular sieve and polymer (e.g., polysilane; urea resin; polystyrene; phenol resin; polypropylene; cellulose; polyurethane; polyamide; polyester; polyethylene; polymethylpentene; polybutene; polybutadiene; polyisobutylene; fluorine resin such as polytetrafluoroethylene and the like; natural rubber; styrene-butadiene rubber; butyl rubber etc.). Of these, a nickel-molybdenum catalyst supported by HY zeolite is preferable. The content of the metal in the supported metal catalyst (B) is 0.1 to 15 wt %, preferably 0.5 to 5 wt %, of the whole weight of the supported metal catalyst (B).

The solvent to be used for continuous hydrogenation is not particularly limited as long as the reaction proceeds and, for example, alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), nitriles (e.g., acetonitrile and the like), carboxylic acids (e.g., acetic acid and the like), water or a mixture thereof can be mentioned, with preference given to a mixed solvent of water and tetrahydrofuran.

An acid (e.g., formic acid, acetic acid, propionic acid, trifluoroacetic acid, citric acid, methanesulfonic acid, benzenesulfonic acid, p-toluenesulfonic acid, trifluoromethanesulfonic acid, hydrochloric acid, sulfuric acid, nitric acid and the like) may be mixed with the solvent. As the acid, propionic acid is preferable. An acid in an amount of generally 0.1 to 50 molar equivalents, preferably 0.5 to 15 molar equivalents, relative to compound (III) or a salt thereof may be mixed.

The concentration of compound (III) or a salt thereof dissolved in the solvent is generally 1 to 20 wt %, preferably 3 to 10 wt %.

The reaction temperature is generally 40 to 100° C., preferably 50 to 70° C.

The amount of hydrogen to be supplied to a fixed bed reactor is generally 1 to 10 molar equivalents relative to the supply amount of compound (III) or a salt thereof. The hydrogenation may be generally performed under pressurization at 0.01 to 1 MPa, preferably 0.01 to 0.3 MPa. The hydrogenation may be performed by continuously supplying a mixed gas of hydrogen and nitrogen into a fixed bed reactor. The hydrogen concentration is 1 to 15 vol %, particularly preferably 3 to 7 vol %.

As the feeding rate of the solution of compound (III) or a salt thereof to a fixed bed reactor, the weight hourly space velocity (WHSV) calculated from the quotient of the supply amount per hour (kg/hr) of compound (III) or a salt thereof and the weight (kg) of supported metal catalyst (B) filled in the fixed bed reactor is generally 0.01 to 1 h$^{-1}$, preferably 0.03 to 0.1 h$^{-1}$.

As the fixed bed reactor, a trickle bed reactor in which a solution of compound (III) or a salt thereof and a mixed gas of hydrogen and nitrogen is introduced from the upper part of the fixed bed reactor and flowed downward is preferable from the aspects of suppression of abrasion of the catalyst due to the trembling of the catalyst.

For the continuous hydrogenation in Step 4, a reaction apparatus similar to the one shown in FIG. 1 can be used.

The hydrolysis can be performed in the presence of an acid or a base. Examples of the acid include inorganic acid (hydrochloric acid, sulfuric acid, nitric acid, phosphoric acid, boric acid and the like), organic carboxylic acid (formic acid, acetic acid, propionic acid and the like), organic sulfonic acid (methanesulfonic acid, benzenesulfonic acid, p-toluenesulfonic acid, trifluoromethanesulfonic acid and the like) and the like. The amount of the acid to be used is about 0.1 to about 10 mol, preferably about 0.1 to about 5 mol, per 1 mol of compound (III). Examples of the base include inorganic bases such as sodium hydroxide, potassium hydroxide and the like, basic salts such as sodium carbonate, potassium carbonate, cesium carbonate, sodium hydrogen carbonate etc., and the like. The amount of the base to be used is about 0.1 to about 10 mol, preferably about 0.1 to about 5 mol, per 1 mol of compound (III).

The hydrolysis is advantageously performed using a solvent inert to the reaction. While such solvent is not particularly limited as long as the reaction proceeds, alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), amides (e.g., N,N-dimethylformamide, N,N-dimethylacetamide and the like), carboxylic acids (e.g., acetic acid and the like), water and a mixture thereof can be mentioned. The amount of the solvent to be used is generally about 1 to about 100 ml, preferably about 1 to about 50 ml, per 1 g of compound (III).

The reaction temperature is generally about −20° C. to about 100° C., preferably about 0° C. to about 50° C. The reaction time is generally about 1 to about 48 hr, preferably about 1 to about 24 hr.

Step 5

Compound (VI) or a salt thereof can be produced by subjecting compound (IV) or a salt thereof to a reaction with compound (V) or a salt thereof.

The amount of compound (V) to be used is preferably about 1 to about 10 mol, more preferably about 1 to about 5 mol, per 1 mol of compound (IV).

This reaction is advantageously performed using a solvent inert to the reaction. While such solvent is not particularly limited as long as the reaction proceeds, alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), acid nitriles (e.g., acetonitrile, propionitrile and the like), water and a mixture thereof can be mentioned. The amount of the solvent to be used is generally 1 to 100 ml, preferably 1 to 50 ml, per 1 g of compound (IV).

This reaction is preferably performed in the presence of a base. Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as diisopropylethylamine, triethylamine, tripropylamine, tributylamine, cyclohexyldimethylamine, 4-N,N-dimethylaminopyridine, N,N-dimethylaniline, N-methylpiperidine, N-methylpyrrolidine, N-methylmorpholine and the like, and a mixture thereof and the like. The amount of the base to be used is about 0.01 to about 10 mol, preferably about 0.1 to about 5 mol, per 1 mol of compound (IV).

The reaction can also be carried out in the co-presence of crown ether. As the crown ether, for example, 15-crown-5-ether, 18-crown-6-ether and the like can be mentioned. The amount of the crown ether to be used is about 1 to about 10 mol, preferably about 1 to about 5 mol, per 1 mol of compound (IV).

The reaction time is generally about 30 min to about 24 hr, preferably about 30 min to about 8 hr. The reaction temperature is generally about 0° C. to about 100° C., preferably about 10° C. to about 50° C.

Step 6

Compound (VIII) or a salt thereof can be produced by reacting compound (VI) or a salt thereof with compound (VII) or a salt thereof, and reducing the imine formed. Alternatively, compound (VIII) or a salt thereof can be produced without isolating the imine formed by performing the reaction of compound (VI) or a salt thereof with compound (VII) or a salt thereof in the presence of a reducing agent.

This reaction can be performed according to the conventional reaction conditions known as reductive amination reaction. For example, the reaction can be performed according to the method described in Jikken Kagaku Koza (Courses in Experimental Chemistry), vol. 14-III, pages 1380-1385 (Maruzen Co., Ltd.).

The amount of compound (VII) to be used is preferably about 1 to about 10 mol, more preferably about 1 to about 5 mol, per 1 mol of compound (VI).

This reaction is advantageously carried out using a solvent inert to the reaction. While the solvent is not particularly limited as long as the reaction proceeds, and alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), water and a mixture thereof can be mentioned. The amount of the solvent to be used is generally 1 to 100 ml, preferably 1 to 50 ml, per 1 g of compound (VI).

The reaction time is generally about 0.5 to about 24 hr, preferably about 0.5 to about 10 hr. The reaction temperature is generally about −50° C. to about 100° C., preferably about −10° C. to about 50° C.

As the reducing agent, sodium borohydride, sodium cyanoborohydride, sodium triacetoxyborohydride and the like can be used. The amount of the reducing agent to be used is preferably about 0.2 to about 10 mol, more preferably about 0.2 to about 5 mol, per 1 mol of compound (VI).

The reduction can also be performed by catalytic hydrogenation.

The catalytic hydrogenation can be performed in the presence of a hydrogen source and a metal catalyst. Examples of the metal catalyst include palladium catalyst (e.g., palladium carbon, palladium hydroxide carbon, palladium oxide and the like), nickel catalyst (e.g., Raney-nickel and the like), platinum catalyst (e.g., platinum oxide, platinum carbon and the like), rhodium catalyst (e.g., rhodium carbon and the like), cobalt catalyst (e.g., Raney-cobalt and the like) and the like. Of these, palladium carbon or Raney-nickel is preferable. The amount of the metal catalyst to be used is about 0.01 to about 10 mol, preferably about 0.01 to about 5 mol, per 1 mol of compound (VI).

As the hydrogen source, hydrogen gas, formic acid, ammonium formate, triethylammonium formate, sodium phosphinate, hydrazine and the like can be mentioned. When a hydrogen source other than hydrogen gas is used, a compound of a hydrogen source is used in about 1 to about 100 mol, preferably about 1 to about 50 mol, more preferably about 1 to about 10 mol, for example, about 1 to about 5 mol, per 1 mol of compound (VI).

The reduction is advantageously performed using a solvent inert to the reaction. Such solvent is not particularly limited as long as the reaction proceeds, and alcohols (e.g., methanol, ethanol, propanol, butanol and the like), hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), water and a mixture thereof can be mentioned. The amount of the solvent to be used is generally 1 to 100 ml, preferably 1 to 50 ml, per 1 g of compound (VI).

The reaction time is generally about 0.5 to about 24 hr, preferably about 0.5 to about 10 hr. The reaction temperature is generally about −50° C. to about 100° C., preferably about −20° C. to about 50° C.

EXAMPLES

The present invention is explained in detail in the following by referring to Reference Examples and Examples, which are not to be construed as limitative.

In the following Reference Examples and Examples, the "room temperature" generally means about 10° C. to about 35° C., but it is not particularly strictly limited. Unless otherwise specified, "%" means weight %. The yield is in mol/mol %. For $^1$H-NMR spectrum, tetramethylsilane (TMS) was used as the internal standard, and Bruker AVANCEIII500 (500 MHz) were used for the measurement.

In the Examples, abbreviations mean as indicated below. s: singlet, d: doublet, dd: double doublet, ddd: double double doublet, t: triplet, m: multiplet, brs: broad singlet, J: coupling constant, Hz: Hertz, THF: tetrahydrofuran, WHSV: Weight Hourly Space Velocity.

Example 1

4-(2-fluorophenyl)-2-(iminomethyl)-4-oxobutanenitrile

A stainless steel SUS316 high pressure reactor (trickle bed reactor, inner diameter 12 mm, length 213 mm) was filled with 15 g of a 1% palladium alumina catalyst. In a 200 mL glass container separately prepared, [2-(2-fluorophenyl)-2-oxoethyl]propanedinitrile (10.0 g, 46.1 mmol) was dissolved in THF (190.0 g) to prepare a reaction solution having a concentration of 5%. Hydrogen was fed at a flow rate of 50 mL/min and the reaction solution was fed at a flow rate of 1.0 mL/min (WHSV: 0.19 h$^{-1}$) into the high pressure reactor filled with the catalyst, continuous hydrogenation was performed at reactor inside temperature 65° C., inside pressure 8.0-9.0 bar (0.8-0.9 MPa), and the reaction mixture was recovered for 3.5 hr in total. The reaction mixture was concentrated to dryness under reduced pressure to give the title compound as a crude product. The obtained crude product was suspended in ethyl acetate (30 mL)/n-hexane (60 mL) mixed solution and the suspension was stirred for 0.5 hr. The solid was collected by suction, and washed with ethyl acetate/n-hexane mixed solution (½ (v/v), 30 mL). Drying under reduced pressure at room temperature gave the title compound (6.8 g, yield 72.4%).

Example 2

5-(2-fluorophenyl)-1H-pyrrole-3-carbonitrile

A stainless steel SUS316 high pressure reactor (trickle bed reactor, inner diameter 9 mm, length 490 mm) was filled with 12 g of a 1% palladium alumina catalyst. In a 1500 mL glass container separately prepared, [2-(2-fluorophenyl)-2-oxoethyl]propanedinitrile (60.0 g, 296.8 mmol) was dissolved in a mixture of THF (1122.2 g) and acetic acid (17.8 g, 296.8 mmol) to prepare a reaction solution having a concentration of 5%. Hydrogen was fed at a flow rate of 25 mL/min and the reaction solution was fed at a flow rate of 0.24 mL/min (WHSV: 0.05 h$^{-1}$) into the high pressure reactor filled with the catalyst, and continuous hydrogenation was performed at reactor inside temperature 57-65° C., inside pressure 0.5 bar (0.05 MPa) Continuously-discharged hydrogen gas was separated from the reaction mixture, and the reaction mixture was continuously fed into a stainless steel SUS316 tubular reactor (inner diameter 4.1 mm, length 417 mm) having an outer temperature 60° C. at a flow rate of 0.24 mL/min, and reacted, and the reaction mixture discharged from the reactor outlet was recovered for 100 hr in total. Under reduced pressure, the volume of the reaction mixture was concentrated to 120 mL at not more than 45° C., acetic acid (75 mL)/0.5N hydrochloric acid (225 mL) was added dropwise at an inside temperature of not more than 30° C., and the mixture was stirred at room temperature for 3 hr. The inside temperature was cooled to 0-10° C. and the mixture was stirred at the same temperature for 1 hr. The precipitated crystals were collected by filtration, and washed with THF (36 mL)/water (144 mL) cooled to 5° C. The crystals were dried under reduced pressure at 40° C. until a constant weight was reached to give the title compound (50.5 g, yield 91.5%).

$^1$H-NMR (DMSO-d$_6$, TMS, 500 MHz) δ (ppm): 6.84 (d, J=1.7 Hz, 1H), 7.1-7.3 (m, 3H), 7.3-7.4 (m, 1H), 7.5-7.6 (m, 1H), 9.3 (br, 1H).

Example 3

5-(2-fluorophenyl)-1H-pyrrole-3-carbonitrile

A stainless steel SUS316 high pressure reactor (trickle bed reactor, inner diameter 25 mm, length 1200 mm) was filled with 100 g of a 1% palladium alumina catalyst. In a 2000 mL glass container separately prepared, [2-(2-fluorophenyl)-2-oxoethyl]propanedinitrile (14.56 g, 72.0 mmol) was dissolved in a mixture of THF (189.12 g) and acetic acid (4.32 g, 72.0 mmol) to prepare a reaction solution having a concentration of 7%. Hydrogen was fed at a flow rate of 300 mL/min and the reaction solution was fed at a flow rate of 1.59 mL/min (WHSV: 0.06 h$^{-1}$) into the high pressure reactor filled with the catalyst, and continuous hydrogenation was performed at reactor inside temperature 85° C., inside pressure 3.0 bar (0.3 MPa). Continuously-discharged hydrogen gas was separated from the reaction mixture, the reaction mixture at a flow rate of 1.59 mL/min was continuously mixed with acetic acid/THF mixture (weight ratio 8:2, flow rate 0.112 mL/min), the mixture was continuously fed into a continuous stirred-tank reactor (inside volume 400 mL, number of reactors, 2) and reacted at an inside temperature of 60° C., and the reaction mixture discharged from the reactor outlet was recovered (200 g in total). Under reduced pressure, the volume of the reaction mixture was concentrated to 44 mL at not more than 45° C., acetic acid (18.2 mL)/0.5N hydrochloric acid (54.6 mL) was added dropwise at room temperature over 1 hr, and the mixture was stirred at room temperature for 3 hr. The inside temperature was cooled to 0-5° C. and the mixture was stirred at the same temperature for 1 hr. The precipitated crystals were collected by filtration, and washed with THF (8.7 mL)/water (34.9 mL) cooled to 5° C. The crystals were dried under reduced pressure at 40° C. until a constant weight was reached to give the title compound (11.5 g, yield 85.8%).

Example 4

5-(2-fluorophenyl)-1H-pyrrole-3-carbaldehyde

In a four-necked flask, 5-(2-fluorophenyl)-1H-pyrrole-3-carbonitrile (10.0 g, 53.71 mmol) and THF (30 mL) were added and dissolved, and acetic acid (50 mL) and water (10 mL) were added. After substitution with nitrogen gas, Raney-nickel (Kawaken Fine Chemicals Co., Ltd., NDHT-90, 5 mL) was added. Then, the mixture was vigorously stirred under a hydrogen atmosphere at inside temperature 15-25° C. for about 4 hr. After substitution with nitrogen gas, Raney-nickel was filtered off and the residue was washed with ethyl acetate (64 mL). Ethyl acetate (36 mL) was added, 8N aqueous sodium hydroxide solution (87 mL) was added to the filtrate at an inside temperature 10-40° C. to adjust the pH to 6.5-7.5, and the mixture was partitioned. The organic layer was washed with 5% aqueous sodium hydrogen carbonate solution (50 mL) and 5% brine (50 mL). To the organic layer was added 5% brine (50 mL), and the mixture was adjusted to pH 3.0-3.5 by adding 6N hydrochloric acid at room temperature, stirred at room temperature for 10 hr, and partitioned. The organic layer was washed with 5% brine (50 mL), and the reaction mixture was concentrated to about 35 g under reduced pressure at not more than 45° C. Furthermore, ethyl acetate (50 mL) was added to the concentrated solution, and the reaction mixture was concentrated to about 35 g under reduced pressure at not more than 45° C. After stirring at room temperature for 1 hr, n-heptane (50 mL) was added dropwise, and the mixture was stirred at the same temperature for 1 hr. Successively, the mixture was stirred at an inside temperature of 0-10° C. for 1 hr. The precipitated crystals were collected by filtration, and washed with n-heptane (20 mL)/ethyl acetate (10 mL) cooled to 5° C. The crystals were dried under reduced pressure at 50° C. until a constant weight was reached to give the title compound (8.6 g, yield 84.4%). $^1$H-NMR (DMSO-d$_6$, TMS, 500 MHz) δ (ppm): 6.91 (d, J=1.6 Hz, 1H), 7.21-7.31 (m, 3H), 7.75-7.80 (m, 2H), 9.76 (s, 1H), 12.17 (brs, 1H).

Example 5

5-(2-fluorophenyl)-1H-pyrrole-3-carbaldehyde

A stainless steel SUS316 high pressure reactor (trickle bed reactor, inner diameter 12.7 mm, length 450 mm) was filled with 8.5 g of a 15% nickel-0.5% molybdenum HY zeolite catalyst. In a 2000 mL glass container separately prepared, 5-(2-fluorophenyl)-1H-pyrrole-3-carbonitrile (28.10 g, 150.9 mmol) was dissolved in a mixture of THF (472.25 g), propionic acid (33.50 g, 452.2 mmol) and water (28.10 g, 452.2 mmol) to prepare a reaction solution having a concentration of 5%. Hydrogen was fed at a flow rate of 5 mL/min, nitrogen was fed at a flow rate of 95 mL/min and the reaction solution was fed at a flow rate of 0.17 mL/min (WHSV: 0.054 h$^{-1}$) into the high pressure reactor filled with the catalyst, continuous hydrogenation was performed at reactor inside temperature 50-60° C., inside pressure 1.0 bar (0.1 MPa), and the reaction mixture discharged from the reactor outlet was recovered for 60 hr in total. Under reduced pressure, the reaction mixture was concentrated to 281.0 g at not more than 45° C., ethyl acetate (300 mL) and water (275 mL) were added to the concentrated solution, the mixture was adjusted to pH 6.8 by adding 8N aqueous sodium hydroxide solution at an inside temperature of 20° C. and partitioned. The organic layer was washed with 5% aqueous sodium hydrogen carbonate solution (150 mL) and saturated brine (150 mL). To the organic layer was added water (150 mL), and the mixture was adjusted to pH 3.4 by adding 6N hydrochloric acid at 20° C., stirred at 20° C. for 2 hr and partitioned. The organic layer was washed with saturated brine (150 mL) and the reaction mixture was concentrated to about 102.4 g under reduced pressure at 40° C. Furthermore, ethyl acetate (150 mL) was added to the concentrated solution, and the reaction mixture was concentrated to 99.7 g under reduced pressure at 40° C. After stirring at 20° C. for 1 hr, n-heptane (150 mL) was added dropwise at 20° C. over 40 min and the mixture was stirred at 20° C. for 1 hr. Successively, the mixture was stirred at an inside temperature of 0-10° C. for 1 hr. The precipitated crystals were collected by filtration, washed with n-heptane (60 mL)/ethyl acetate (30 mL) cooled to around 5° C., and dried under reduced pressure at 45° C. until a constant weight was reached to give the title compound (22.45 g, yield 78.6%).

Example 6

5-(2-fluorophenyl)-1-(pyridin-3-ylsulfonyl)-1H-pyrrole-3-carbaldehyde 5-(2-Fluorophenyl)-1H-pyrrole-3-carbaldehyde (7.0 g, 37.00 mmol), N,N-dimethylpyridine-4-amine (0.902 g, 7.38 mmol), diisopropylethylamine (6.69 g, 51.80 mmol) and acetonitrile (28 mL) were added to a four-necked flask, then pyridine-3-sulfonyl chloride (7.89 g, 44.42 mmol) was added dropwise, and the mixture was washed well with acetonitrile (3.5 mL). The mixture was stirred at an inside temperature of 40-50° C. for about 1 hr, and cooled to an inside temperature of 25-35° C., and water (21 mL) was added dropwise at the same temperature. Then the mixture was adjusted to pH 4-5 at room temperature with 0.5N hydrochloric acid (8 mL), and water (41 mL) was added dropwise at room temperature. After stirring at room temperature for 30 min, the inside temperature was cooled to 0-10° C., and the mixture was stirred for 1 hr. The precipitated crystals were collected by filtration, washed with acetonitrile (14 mL)/water (28 mL) cooled to 5° C., and dried under reduced pressure at 50° C. until a constant weight was reached to give the title compound (10.6 g, yield 87.0%).

$^1$H-NMR (CDCl$_3$, TMS, 500 MHz) δ (ppm): 6.68 (d, J=1.6 Hz, 1H), 7.02 (dd, J=8.2, 8.2 Hz, 1H), 7.14-7.19 (m, 2H), 7.38 (dd, J=8.2, 4.9 Hz, 1H), 7.44-7.48 (m, 1H), 7.72 (ddd, J=8.2, 2.5, 1.6 Hz, 1H), 8.17 (d, J=1.9 Hz, 1H), 8.59 (d, J=1.9 Hz, 1H), 8.82 (dd, J=4.7, 1.6 Hz, 1H), 9.90 (s, 1H).

Example 7

1-[5-(2-fluorophenyl)-1-(pyridin-3-ylsulfonyl)-1H-pyrrol-3-yl]-N-methanamine fumarate To a nitrogen-substituted four-necked flask were added N,N-dimethylacetamide (10 mL) and sodium borohydride (0.275 g, 7.27 mmol) and dissolved therein (solution A). To another nitrogen-substituted four-necked flask were added 5-(2-fluorophenyl)-1-(pyridin-3-ylsulfonyl)-1H-pyrrole-3-carbaldehyde (5.0 g, 15.14 mmol) and methanol (22.5 mL), then, a methanol solution (1.59 g, 21.04 mmol) of 40% methylamine was added dropwise at room temperature, and the mixture was stirred at room temperature for about 1 hr. After cooling to an inside temperature of 0-10° C., solution A prepared earlier was added dropwise at the same temperature, and the mixture was stirred at an inside temperature of 0-10° C. for 1 hr. 1N aqueous hydrochloric acid solution (35 mL) was added dropwise at an inside temperature of not more than 20° C., and the mixture was stirred at an inside temperature of 20±5° C. for 2 hr. 12.5% Aqueous ammonia (30 mL) and ethyl acetate (50 mL) were added and the mixture was partitioned. The aqueous layer was extracted with 5% brine (25 mL) and ethyl acetate (25 mL). The combined organic layer was washed twice with 5% brine (30 mL). The organic layer was concentrated to about 12.5 mL, ethyl acetate (35 mL) was added, and the mixture was concentrated again to about 19 mL. N,N-Dimethylacetamide (29 mL) was added, and the mixture was heated to an inside temperature of 40° C., and fumaric acid (0.878 g, 7.56 mmol) was added. After stirring at an inside temperature of 40-50° C. for 30 min, fumaric acid (0.878 g, 7.56 mmol) was added again, and the mixture was washed well with N,N-dimethylacetamide (1 mL). After stirring at an inside temperature of 40-50° C. for 30 min, ethyl acetate (15 mL) was added dropwise, and the mixture was stirred at an inside temperature of 45±5° C. for 30 min. After cooling, the mixture was stirred at room temperature for about 1 hr. The precipitated crystals were collected by filtration, washed with ethyl acetate (3.75 mL)/N,N-dimethylacetamide (3.75 mL) and successively with ethyl acetate (15 mL) to give a crude product (wet material).

The crude product (wet material, total amount) obtained above was suspended in a mixed solution (2:3, 75 mL) of methanol and water at room temperature, and dissolved at an inside temperature of 60-70° C. Activated carbon SHI-RASAGI A (registered trademark) (0.15 g) was added, and the mixture was washed well with a mixed solvent of methanol and water (2:3, 2 mL). After stirring for about 1 hr, the mixture was filtered and washed with a mixed solvent of methanol and water (2:3, 8 mL). The combined filtrates were dissolved again at an inside temperature of 60-70° C., cooled to an inside temperature of 0-10° C., and stirred at the same temperature for 1 hr. The precipitated crystals were collected by filtration, and washed with a mixed solution of methanol and water (2:3, 10 mL). The crystals were dried under reduced pressure at an outer temperature of 50° C. to give the title compound (4.63 g, isolation yield 72.7%).

$^1$H-NMR (DMSO-$d_6$, TMS, 500 MHz) δ (ppm): 2.48 (s, 3H), 3.95 (s, 2H), 6.51 (s, 2H), 6.53 (d, J=1.6 Hz, 1H), 7.11 (ddd, J=7.6, 7.6, 1.6 Hz, 1H), 7.21-7.25 (m, 2H), 7.51-7.55 (m, 1H), 7.62 (dd, J=8.2, 5.0 Hz, 1H), 7.80 (brs, 1H), 7.90 (ddd, J=8.2, 2.5, 1.6 Hz, 1H), 8.57 (d, J=1.9 Hz, 1H), 8.89 (dd, J=4.7, 1.6 Hz, 1H), 10.53 (brs, 3H).

Example 8

Long-time continuous reaction synthesis of 5-(2-fluorophenyl)-1H-pyrrole-3-carbonitrile Using the conditions shown in Example 2, long-time continuous reaction synthesis of 5-(2-fluorophenyl)-1H-pyrrole-3-carbonitrile was performed, and a catalyst lifetime confirmation test of a 1% palladium alumina catalyst was performed. The activity of the catalyst did not decrease even after the reaction time of 720 hr in total. The results are shown in Table 1.

TABLE 1

| | reaction time | | |
|---|---|---|---|
| | 240 hr | 480 hr | 720 hr |
| reaction conversion rate[1] (%) | 98.9 | 99.5 | 99.8 |
| reaction selectivity[2] (%) | 97.1 | 97.7 | 97.8 |

[1] reaction conversion rate = 100-residual ratio (%) of [2-(2-fluorophenyl)-2-oxoethyl]propanedinitrile
[2] reaction selectivity = generation rate (%) of 5-(2-fluorophenyl)-1H-pyrrole-3-carbonitrile/reaction conversion rate (%) × 100

Reference Example 5-(2-fluorophenyl)-1H-pyrrole-3-carbonitrile

In a four-necked flask, [2-(2-fluorophenyl)-2-oxoethyl]propanedinitrile (45.0 g, 222.6 mmol) and THF (392.1 g) were added and dissolved therein. After substitution with nitrogen gas, 50% water-containing 10% palladium carbon catalyst (3.542 g, dry weight basis 1.575 g) was added, and the mixture was washed with THF (8.0 g). After successive substitution with hydrogen, the mixture was reacted under hydrogen pressure 0.00-0.02 MPa at an inside temperature 35-45° C. until the starting material became 3% or below (reaction time: 13 hr). The catalyst was filtered off and washed with THF (120.0 g). Under reduced pressure, the reaction mixture was concentrated to 90 g at not more than 45° C., and acetic acid (90.0 mL) was added. The mixture was stirred at an inside temperature of 50-65° C. for 1.5 hr. To the reaction mixture was added dropwise 0.5N hydrochloric acid (405.0 mL) at an inside temperature of 15-25° C., and the mixture was stirred at the same temperature for 30 min. Successively, the inside temperature was cooled to 0-10° C., and the mixture was stirred at the same temperature for 1 hr. The precipitated crystals were collected by filtration, washed with THF (27 mL)/water (108 mL) cooled to 5° C., and dried under reduced pressure at 40° C. until a constant weight was reached to give the title compound (32.4 g, yield 78.2%).

INDUSTRIAL APPLICABILITY

According to the method of the present invention, a 3-cyanopyrrole compound can be produced efficiently in a high yield as compared to conventional batch methods. Compound (II), 3-cyanopyrrole compound (III) and compound (IV) obtained by the method of the present invention may be useful as intermediates for producing sulfonylpyrrole compound (VIII).

Sulfonylpyrrole compound (VIII) obtained by the method of the present invention may be useful as an acid secretion inhibitor (proton pump inhibitor).

This application is based on patent application No. 2015-131610 filed in Japan, the entire contents of which are incorporated by reference herein.

EXPLANATION OF SYMBOLS 1 feed solution
2 feed pump
3 gas-liquid mixing zone
4 jacket for heating reactor
5 trickle bed reactor (filled with catalyst)
6 mass flow controller
7 chamber
8 pressure regulating valve
9 reaction mixture recovery container
10 hydrogen exhaust device
11 hot-water bath (for regulating reactor temperature)
12 tubular reactor
13 hydrogen tank
14 gas-liquid separator
15 continuous stirred-tank reactor

The invention claimed is:

1. A method for producing a compound represented by the formula

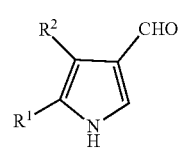

(IV)

wherein R$^1$ is an optionally substituted hydrocarbon group or an optionally substituted heterocyclic group, and R$^2$ is a hydrogen atom, an optionally substituted hydrocarbon group, an optionally substituted heterocyclic group, a chlorine atom or a fluorine atom, or a salt thereof, comprising subjecting a compound represented by the formula

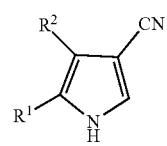

(III)

wherein each symbol is as defined above, or a salt thereof to a reduction reaction, and then to hydrolysis, wherein the reduction reaction is a continuous hydrogenation in a fixed bed reactor filled with a supported metal catalyst.

2. The production method according to claim 1 wherein the supported metal catalyst comprises a metal selected from the group consisting of molybdenum (Mo), nickel (Ni), palladium (Pd), platinum (Pt), chromium (Cr), tungsten (W) and a combination thereof.

3. The production method according to claim 1 wherein the supported metal catalyst has a metal content of 0.1-15 wt % relative to the whole weight of the supported metal catalyst.

4. The production method according to claim 1 wherein the metal of the supported metal catalyst is supported by zeolite as a carrier.

5. The production method according to claim 4 wherein the zeolite is HY zeolite.

6. The production method according to claim 1 wherein the hydrogenation is performed in a solvent containing an acid.

7. The production method according to claim 6 wherein the acid is propionic acid.

8. The production method according to claim 6 wherein the acid is mixed in a proportion of 0.1-50 molar equivalents relative to the compound represented by the formula (III) or a salt thereof.

9. The production method according to claim 6 wherein the solvent is a mixed solvent of water and tetrahydrofuran.

10. The production method according to claim 1 wherein the hydrogenation is performed at 40-100° C.

11. The production method according to claim 1 wherein the hydrogenation is performed under a pressure of 0.01-1 MPa.

12. The production method according to claim 1 wherein the hydrogenation is performed at a hydrogen concentration of 1-15 vol %.

13. The production method according to claim 1 wherein the compound represented by the formula (III) or a salt thereof is supplied into the fixed bed reactor at WHSV (weight hourly space velocity) of 0.01-1 h$^{-1}$.

14. The production method according to claim 1 wherein the compound represented by the formula (III) or a salt thereof is supplied into the fixed bed reactor at a concentration of 1-20 wt % in a solution.

15. The production method according to claim 1 wherein the fixed bed reactor is a trickle bed reactor.

16. The production method of claim 1, wherein the compound of Formula (IV) is:

the compound of Formula (III) is:

and
the fixed bed reactor filled with a supported metal catalyst is a nickel-molybdenum catalyst supported by HY zeolite.

17. A method for producing a compound represented by the formula

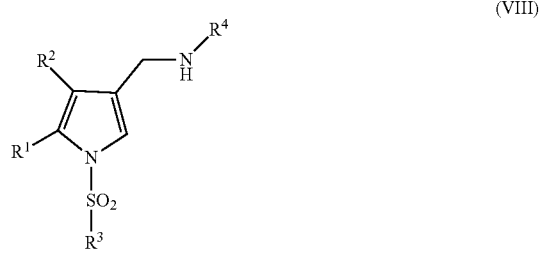

wherein R$^1$ is an optionally substituted hydrocarbon group or an optionally substituted heterocyclic group, R$^2$ is a hydrogen atom, an optionally substituted hydrocarbon group, an optionally substituted heterocyclic group, a chlorine atom or a fluorine atom, R$^3$ is an optionally substituted hydrocarbon group or an optionally substituted heterocyclic group, and R$^4$ is an alkyl group, or a salt thereof, comprising (1) subjecting a compound represented by the formula

wherein each symbol is as defined above, or a salt thereof to a reduction reaction, and then to hydrolysis to give a compound represented by the formula

wherein each symbol is as defined above, or a salt thereof, wherein the reduction reaction is a continuous hydrogenation in a fixed bed reactor filled with a supported metal catalyst, (2) reacting the obtained compound with a compound represented by the formula $$R^3—SO_2—X \quad (V)$$

wherein R$^3$ is as defined above, and X is a leaving group, or a salt thereof to give a compound represented by the formula

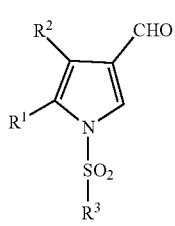
(VI)
wherein each symbol is as defined above, or a salt thereof, and
(3) reacting the obtained compound with a compound represented by the formula
 (VII)
wherein $R^4$ is as defined above, or a salt thereof.
* * * * *